United States Patent [19]

Perdelwitz, Jr. et al.

[11] Patent Number: 5,030,500

[45] Date of Patent: Jul. 9, 1991

[54] THERMOPLASTIC MATERIAL CONTAINING TOWEL

[75] Inventors: Lee E. Perdelwitz, Jr., Tacoma; Gustav O. Pfeiffer, Auburn; Amar N. Neogi, Seattle; Ron H. Iff, Puyallup; Haresh R. Mehta, Federal Way, all of Wash.

[73] Assignee: Weyerhaeuser Company, Tacoma, Wash.

[21] Appl. No.: 384,218

[22] Filed: Jul. 21, 1989

[51] Int. Cl.⁵ .................................................. B32B 3/10
[52] U.S. Cl. .................................... 428/137; 428/131; 428/171; 428/172; 428/192; 428/284; 428/296; 428/913
[58] Field of Search ............... 428/171, 172, 137, 138, 428/289, 296, 192, 913, 284, 131

[56] References Cited

U.S. PATENT DOCUMENTS

| | | | |
|---|---|---|---|
| 4,239,792 | 12/1980 | Ludwa | 128/156 |
| 4,469,734 | 9/1984 | Minto et al. | 428/134 |
| 4,886,697 | 12/1989 | Perdelwitz et al. | 428/280 |

Primary Examiner—James J. Bell
Attorney, Agent, or Firm—Klarquist, Sparkman, Campbell, Leigh & Whinston

[57] ABSTRACT

A durable launderable towel has a thermobonded core of thermoplastic and other fibers. The towel has at least one cover sheet which is preferably formed with apertures. The towel is also densified in a field pattern and is typically densified at the peripheral edge. Embossing is preferably used to form these densified areas. The combination of thermobonding the core, embossing and the use of apertured cover sheets results in a towel having the softness, drape and feed approaching that of cloth. By controlling the embossing on the wiping surfaces of the towel, a towel with surfaces having different wipe dry characteristics and textures can be produced.

6 Claims, 2 Drawing Sheets

THERMOPLASTIC MATERIAL CONTAINING TOWEL

BACKGROUND OF THE INVENTION

The present invention relates to absorbent towels which contain thermoplastic materials and more specifically to durable washable plural layer composite towels which include an absorbent layer formed from a mixture of thermoplastic and other nonthermoplastic fibers, such as wood pulp fibers.

BACKGROUND ART

Many prior art devices exist for wiping liquids, dirt, soil, grease, dust and the like from surfaces. These surface wiping devices can generally be referred to as towels.

Among the most common surface wiping devices are rags (scraps of woven fabrics) and cloth towels. Durable devices used in restaurants include terry and ribbed terry towels of varying sizes. These towels are woven textile fabric and are generally made from cotton or blends of cotton and synthetic fibers. Bar towels are typically of a woven textile sometimes referred to as "linen", but which are actually made from cotton or cotton blends. Although strong and absorbent, these products are relatively expensive. By their nature, these cloth towels generally leave the wiped surface wet; the residual water usually being present in the form of large drops which contribute to streaking and spotting. Durable cloth bar towels of this type have excellent feel. However, durable products of cloth are laundered many times and reused. However, such towels may become so soiled with grease or other substances that laundering is unlikely to clean the towels and remove stains. In such a case, the towels are typically replaced with costly new towels.

In addition to cloth towels, disposable towels have also been used. Disposable, as used herein, refers to devices intended to be used at most a few times and then discarded. As such, the concept of a disposable product excludes the laundering of the device, although disposable products may be rinsed once or several times during their effective life and reused. Such rinsing is not to be considered to be laundering as used in connection with the concept of durable devices. In contrast, durable towels are suitable for laundering and reuse.

One type of disposable towel is described in U.S. Pat. No. 4,239,792 of Ludwa. The towels of this patent comprise a core sandwiched between outer surface wiping elements. The core is described as preferably being of a paper-based material, with a mass of nonwoven or woven fabric or foam materials also being mentioned as possibilities. Other core materials mentioned in this patent include bonded air felts formed from wood pulp fibers; single ply and multi-ply nonwoven or woven fabric; and absorbent cellulose, polyurethane, and polyester foams. The basis weight of the core is indicated to be from about sixteen to eighty grams per square meter. The outer surface wiping layers are each described as generally being of a single ply of nonwoven fabric, although subelements are also mentioned. Layers of bonded fibers or mechanically entangled fibers are mentioned, with the preferred material being one prepared by a process which tends to provide apertures within the fabric. Sontara ®, a spun-laced nonwoven polyester product from Du Pont Corporation is one specifically mentioned material. The cover and core are laminated together with the patent stating that any conventional method of laminating can be used and specifically mentioning sewing and the use of latex adhesives.

Although relatively inexpensive in comparison to cloth towels, the wipes of the Ludwa patent are specifically described as disposable, which is defined to exclude laundering for reuse. Thus, these wipes lack desired durability for repeated use following laundering.

U.S. Pat. No. 4,469,734 of Minto, et al. describes microfiber web products made from meltblown microfibers. The webs are formed or provided with apertures by, for example, hot needling or by passing the web between differentially speeded rolls. The addition of fibers such as wood pulp to the web is mentioned. These webs are limited in strength and absorbency characteristics. However, one embossing pattern shown in this patent is similar to one specific exemplary embossing pattern utilized in towels of the present invention.

Finally, U.S. patent application Ser. No. 07/188,474 of Perdelwitz, et al., entitled "Thermoplastic Material Containing Absorbent Pad or Other Article", filed Apr. 29, 1988, is incorporated by reference herein in its entirety. The Perdelwitz, et al. patent application describes the manufacture of absorbent articles, including laminated articles having cover sheets and a core formed of thermoplastic and other fibers. A number of suitable commercially available cover sheets are described, including Sontara ®. The resulting laminated product can be embossed at field locations within the boundaries of the product and also can be densified at the edge margins. Example 12 of this patent relates specifically to a towel. Although extremely durable, the towel described in this example is distinguishable in drape and feel from cloth towels.

Therefore, although thermoplastic fibers have been combined with other fibers and used in the manufacture of articles, a need exists for improved towels of this type.

SUMMARY OF THE INVENTION

In accordance with one aspect of the present invention, a core or absorbent layer for a towel is formed of a mixture of fibers comprising at least one thermoplastic material and other fibers, such as wood pulp fibers. The core is thermobonded together by heating the mixture to a temperature above the melting point of the fibers of at least one thermoplastic material in the mixture. Preferably the core is sandwiched between a pair of cover sheets of a liquid permeable material. Most preferably the cover sheets are of an apertured nonwoven material and the material is embossed with a pattern of embossing areas which, in combination with the apertured cover stock and core, results in a towel with a texture, hand and softness which approximates the feel of natural towels.

The towel may be compressed and densified along its peripheral edge to provide a substantial liquid seal at the edge. The densified edge also adds to the durability of the towel.

An important characteristic of the towel of the present invention is its durability. That is, such towels can be laundered under normal conditions a number of times for reuse. On average, the towels of the present invention are launderable at least about five times while still maintaining their integrity for use. Laundering under normal conditions refers to washing the towels with detergent in commercial or residential-type washing machines and drying these towels in a dryer, typically on low heat. This allows the towels to be cleaned for reuse. Yet, because the towels are of relatively inexpensive materials, in the event they become too soiled or stained for cleaning and, after their useful life, they may be simply replaced without incurring the high relative costs associated with conventional cloth towels.

Accordingly an object of the present invention is to provide improved thermoplastic material containing towels.

Another object of the present invention is to provide strong towels of such materials which are relatively strong and durable for laundering and reuse, yet are relatively inexpensive.

A further object of the present invention is to provide towels of such materials which have a hand, drape and feel which approximates cloth.

Still another object of the present invention is to provide such towels which minimize the leakage of liquids and dust from their edges.

A still further object of the present invention is to provide such towels which can be produced at a cost effective and high volume rate.

These and other objects, features and advantages of the present invention will become apparent with reference to the following detailed description and drawings.

DETAILED DESCRIPTION OF THE PREFERRED EMBODIMENT

General Description of Materials

Thermoplastic Fiber Containing Core

Figure 1:
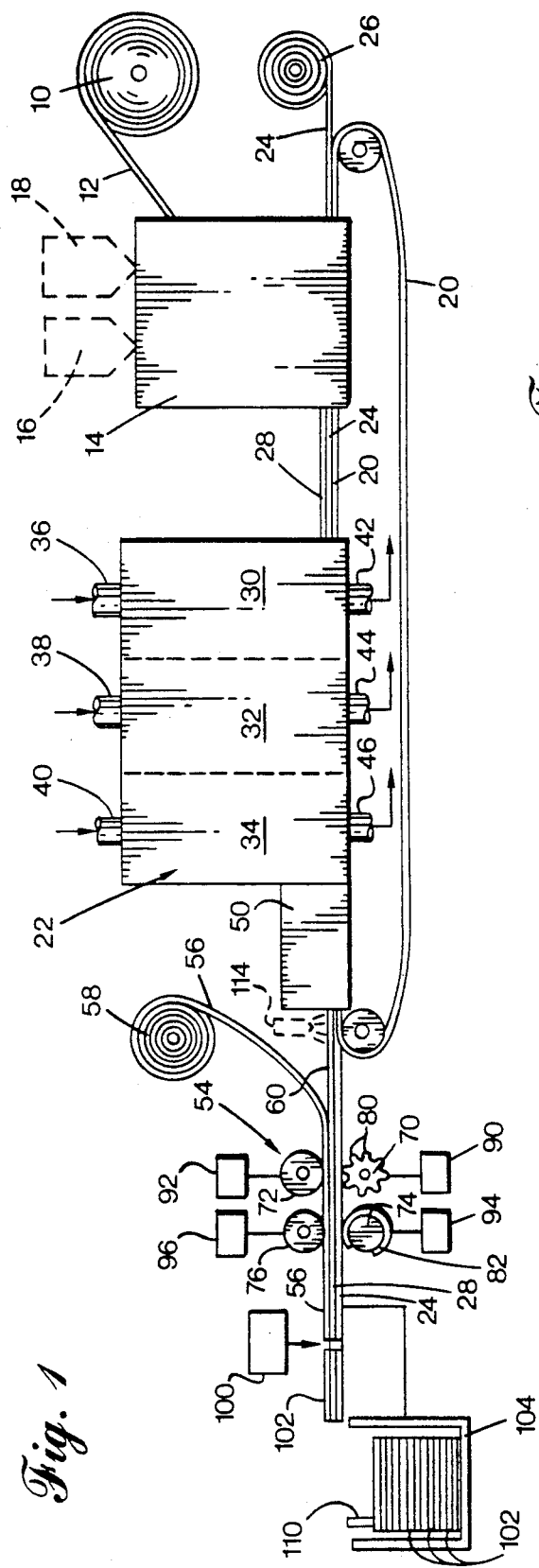
FIG. 1 is a schematic side elevational view of one form of apparatus for manufacturing towels of the present invention.

For purpose of convenience, the thermoplastic fiber containing layer will be referred to herein as a core. However, it will be appreciated that in two layer laminated towels, the core itself respectively comprises one of the outer layers of the towel. Thus, in such a case the core would not be sandwiched between two or more cover layers. Also, the core itself may be laminated, thus being formed of subelements as may the cover sheets.

As previously mentioned, the core is formed from a mixture of at least one thermoplastic material or material containing fiber in combination with one or more other types of fibers. The core forming fibers, on the average, have a length to diameter or cross sectional dimension ratios of greater than 5 and typically have ratios close to 100 or more.

Suitable thermoplastic fibers are typically made from thermoplastic polymers and are commercially available. These thermoplastic fibers have a high surface area to diameter ratio and are capable of melting when subjected to heat. Representative thermoplastic fibers are made from polyethylene, polypropylene, copolymers of ethylene and propylene, and copolymers of propylene and other 1-olefins such as 1-butene, 4-methyl-pentene-1, and 1-hexene. Grafted polyolefins pulps may also be used, in which maleic anhydride or styrene groups are grafted. In some embodiments, the thermoplastic fibers are composed solely of one type of thermoplastic. In other embodiments, the fibers are composed of mixtures of two or more types of thermoplastic fibers. Bicomponent fibers, such as comprised of polyethylene and polypropylene, may also be used. Polyester fibers are still another example of suitable fibers. Cellulose acetate is a further example of a suitable fiber.

Suitable commercially available products for making the thermoplastic fibers include Pulpex ® E-338 from Hercules, Inc., a polyethylene based product; Kodel ® from Eastman Kodak Corporation, a polyester based product; and Vinyon ® from Celanese Corporation.

As explained in greater detail below, assume the thermoplastic materials are comprised of a mixture of more than one type of thermoplastic fibers, such as polyethylene and polyester fibers. In this case, during thermobonding, the core is heated to a temperature sufficient to melt the lower melting point thermoplastic fibers (polyethylene) without melting the higher melting point thermoplastic fibers (polyester). Consequently, the integrity of these latter fibers is preserved and strengthens the resulting core. In addition, by making the polyester fibers of a relatively long length, such as equal to or greater than about one-half inch, cores of enhanced tensile strength are produced.

Preferably, for durable towels, the core has thermoplastic materials in an amount of from about 15%-30% by weight, and other fibers, such as wood pulp, make up the remainder of the mixture. However, greater or lesser percentages of thermoplastic materials may be used, although this affects the drape of this fabric.

As previously mentioned, the fibers mixed with the thermoplastic fibers to form the core may include wood pulp. These fibers are commercially available from a number of companies, including Weyerhaeuser Company, the assignee of the present application. In addition to wood pulp fibers, other nonthermoplastic synthetic and natural staple fibers such as rayon, cotton and the like may be included in the core forming mixture.

Also, depending upon the particular application, other absorbent materials may be added to the mixture. After the mixture is thermobonded, these added materials are substantially retained in place due to the thermobonding. The densified edge sections of the article also help retain these materials in place. Therefore, the tendency of these materials to escape or migrate from the article and into the external environment is reduced. Materials are selected which do not substantially degrade when subject to the temperature conditions that are present during thermobonding. Also by selecting thermoplastic materials with relatively low melting points, thermobonding can be accomplished at a temperature which minimize the possible thermal degradation of these materials. Among the suitable materials that may be included in the mixture are absorbent materials such as desiccants and super absorbent materials. In practice, any absorbent or adsorptive material can be added to the mixture. Representative examples include activated carbon, acid clay, active alumina, diatomaceous earth, silica gels and the like. Relatively newly developed superabsorbent polymers, such as crosslinked polyacrylate commercially available under the brand name "Drytech" from Dow Chemical Company may also be included. Other absorbent substances generally used in the form of a powder can conveniently be fixed in the core in accordance with the process of the present invention.

In addition, oil absorbent materials such as polymers, including polynorbornene, available under the brand name "Norsorex" from C.d.F. Chemie of France, may be included. In addition, deodorizing materials such as odor absorbing, odor masking, odor inhibiting and odor eliminating materials, may be included in the core forming mixture. Examples include baking soda, cedar oil and other fragrances. Again, the thermobonding of the core helps fix these materials in place.

Instead of including these absorbent materials in the core forming mixture prior to bonding, they may be placed on one or both surfaces of the core following the core formation. These materials may be included in an adhesive coating on the core or simply sprayed on the core in liquid form and allowed to dry.

Finally, due to the methods of forming a core and articles of the present invention, cores of widely varying basis weights may be manufactured. For durable towels with a textilelike drape, core basis weights of from about 50 to 150 g/m$^2$ are preferred with a basis weight of about 80 g/m$^2$ being most preferred.

Cover Layer Materials

The facing or covering layers typically comprise a preformed sheet or web and may be of a nonwoven thermoplastic containing material. During manufacture, the core forming mixture is typically deposited on the bottom one of the covering sheets to the desired depth. To prevent melting of the covering sheet during thermobonding, it is selected to have a melting point which is higher than the melting point of the thermoplastic fibers of the core which are to be melted during thermobonding. When the covering sheet and deposited mixture pass through the thermobonder, the core fibers are thermobonded together and to the facing sheet. The top facing or covering sheet may also be passed through the thermobonder. Also, the top covering sheet, as well as the top and bottom covering sheets, may be secured to the core following the thermobonding of the core.

Thus, the selection of the covering sheet material will depend at least in part upon the thermoplastic fibers included in the core and the manufacturing approach. Representative covering sheet materials include thermoplastic coated materials such as rayon which is resin or otherwise coated with a thermoplastic layer, polyolefin materials, spun laced polyester and polypropylene, resin bonded polyester and polypropylene, spun bonded polyester and polypropylene, thermobonded polyester and polypropylene, carded polyester and polypropylene, melt blown polypropylene, polyethylene films of varying densities, polypropylene films, apertured films and other suitable materials apparent to those skilled in the arts.

In addition, if a manufacturing method is employed wherein heated air is pulled through the core and the facing sheet during thermobonding, the facing sheet must be perforated or otherwise breathable.

Some commercially available suitable nonwoven continuous filament products include Cerex®, a nylon material from James River Corporation, Reemay®, a spun bonded polyester material from Intertec Corporation, Sontara®, a spun laced polyester product from Du Pont Corporation, and Chicopee wipe, a spun-laced polyester product from Chicopee Company.

Again, a wide variety of facing sheet materials may be used. These facing sheets are thermoplastic or thermoplastic containing for those applications in which the facing sheet is to be thermobonded to the core. If the facing sheets are secured to the core in another manner, such as by adhesive, then they need not be thermoplastic. Nonwoven materials are exemplary facing sheets because such materials readily allow the passage of liquids to the absorbent core.

Although variable, the most preferred facing or covering sheets for towels have a basis weight of from about 20 to 80 g/m$^2$ and are liquid permeable to permit the passage of liquid to the core. Furthermore, covering sheets of the type prepared by a process which produces apertures in the fabric are especially preferred. When embossed as explained below, these apertured cover stock materials, such as Sontara® and Chicopee wipe, produce an inexpensive towel which has the drape, softness and feel approximating that of bar towels and other textile fabrics.

Manufacturing Method

In one typical approach, the thermoplastic and other fibers to be used in forming the core are blended by any of the known blending methods. Optional absorbent and other additives may also be blended in at this time. Such methods include the preparation of a pulp sheet by conventional paper-making procedures or by conventional dry blending methods. The resulting sheet is then rolled up to form a roll of core forming fibers such as indicated at 10 in FIG. 1. A sheet 12 is fed from roll 10 to a fluff preparation zone 14. At zone 14, the web 12 is formed into a fluff pad by conventional methods such as hammermilling or air forming.

In other suitable approaches, the thermoplastic core forming fibers may be fluffed separately from the other fibers, deposited in a hopper 16, and distributed by an air stream into the fluff preparation zone. In this case, the wood pulp and other fibers are similarly fluffed and deposited in a hopper 18 and distributed by an air stream within the fluff preparation zone for mixing with the thermoplastic fibers from the hopper 16. Absorbent material additives may also be added to hoppers 16 and 18. Vacuum air laying techniques may also be employed. Similarly, pulp sheets can be passed through a hammermill with the thermoplastic fibers being added in a separate step. Thus, the specific manner of forming the mixture of thermoplastic and other fibers that eventually become the core of the article is not critical.

In the illustrated approach, a thermoplastic containing face sheet, such as a breathable, nonwoven, liquid permeable apertured facing sheet web 24 from a roll 26, is positioned on a foraminous screen 20 upstream from the fluff preparation zone 14. As facing sheet 24 passes through the fluff preparation zone, the core forming fibers are deposited on the facing sheet to the desired depth as established in a conventional manner, such as by use of a doctor roll. The unfused core forming fibers, indicated at 28 in FIG. 1, together with the facing sheet 24, are carried by the belt 20 into a thermobonder 22. The thermobonder 22 heats the fibers to a temperature above the melting point of at least one thermoplastic fiber material in the core. For example, the melting point of some types of polyethylene pulp is 122° to 134° C. while the melting point of some types of polypropylene fiber is 160° to 165° C. This heat fuses the core and also bonds the core to the facing sheet. Although calenders, infrared heaters, and other heating devices may be employed to heat fuse the core, the illustrated thermobonder 22 comprises a flow-through dryer. The exact heating conditions, which can be readily ascertained by one skilled in the art, must be determined for the specific fiber blend being used. The time that the core spends within the thermobonder 22 is also readily ascertainable by one skilled in the art. Generally this time ranges from about one hundred milliseconds to one minute depending in part upon the temperature of the thermobonder and the line speed at which the screen is traveling. Thereafter, the core can then be densified at eventual edge margin sections of an article to be formed from the core and otherwise processed as explained below.

Although not required, the thermobonder has three stages 30, 32 and 34. In each stage, heated air enters from a respective inlet 36, 38 and 40. The entering heated air passes successively through the core forming fibers 28, the facing sheet 24, the belt 20 and to a respective exit outlet 42, 44 and 46. A pressure differential is maintained across the traveling materials to draw the heated gas through these materials. For example, the inlets may be pressurized relative to the outlets or a vacuum may be applied to the outlets. The melted thermoplastic material fibers of the core 28 fuse or thermobond the core to itself and also to the face sheet 24. The temperature is such that the face sheet 24 is not melted by the thermobonder 22.

Typical line speeds for the screen 20 are from 100 to 250 feet per minute with 150 feet per minute being a normal operating speed. The thermobonder 22 includes an optional convention oven or apron 50. This oven maintains the temperature of the bonded core and facing as these materials travel toward a feature forming zone 54.

The upper cover sheet 56, which may be identical to the sheet 24, is fed from a roll 58 to the exposed surface 60 of the core. The sheet 56 may instead be placed on top of the core and fed through the thermobonder so as to be bonded to the core as the core is thermobonded.

At feature forming zone 54, the multilayered or composite web is typically bonded or densified along at least a section of the eventual peripheral edge margin of an article to be formed. Typically, the entire eventual peripheral edge margin of the article is densified. In addition, field bonds are also formed within the eventual field of the article intermediate the peripheral edge margin. A number of suitable processes may be used to form these densified areas. These include ultrasonic bonding and adhesive bonding. However, the preferred approach is to emboss these bond areas. To this end, opposed sets of embossing rolls 70, 72 and 74, 76 are positioned as shown. The illustrated roll 70 comprises a field bond feature forming roll having a projecting pattern of field bond forming contacts 80 which press against the face sheet and other layers of the composite material. Roll 72 may comprise a roll with field bond forming contacts, but typically comprises a smooth surfaced anvil roll which is positioned against the top sheet 56. Typically another pair of rolls (not shown) like rolls 70, 72 are used to emboss the top sheet 56 with the feature forming roll located adjacent to and above the sheet 56 and the anvil roll located below the sheet 24. Similarly, roll 74 comprises a peripheral edge margin feature forming roll having contacts 82 arranged to define those sections of the eventual peripheral edge margins of the article which are to be densified. Normally, the entire eventual edge margin of the article is densified by feature forming roll 74. Roll 76 comprises a smooth anvil roll which backs up the feature forming roll.

A conventional temperature control 90, 92, 94 and 96 is provided for each of the respective rolls 70, 72, 74 and 76 for independently controlling the temperature for these rolls (and for other rolls) is used. If the same materials are being used for the backing and facing sheets, typically these rolls are kept at the same temperature. The rolls are typically held at temperatures below the melting point of the core fibers, for example, at 120°-130° C., depending upon the materials. In cases where the top sheet 56 has a relatively low melting point, rolls 72 and 76 may be kept somewhat cooler (i.e. at 80°-110° C. depending upon the material) than rolls 70 and 74 to act as a heat sink to assist in cooling the backing sheet 56 below its melting point.

The temperature of the embossing rolls 70 through 76 is preferably held cooler than the melting point temperatures of both the core 28 and the face sheet 24. By maintaining the core 28 above its thermobonding temperature when it reaches the embossing rolls, the feature forming rolls bring the core temperature below the thermobonding temperature to thermoset or heat seal and compress the peripheral edge margins and field bonds in the pad or other article. Also, the core 28 and cover sheet 24 do not tend to delaminate when embossed with these cooler embossing rolls. The field bond contacts 80 and peripheral margin bond contacts 82 may also be placed on the same roll.

The nip gap between the contacts 80 and the corresponding anvil roll is typically from about two to twelve thousandths of an inch with four to eight thousandths of an inch being preferred. Typically one-quarter inch to one-half inch spacing is provided between the contact and the relief portions of these rolls. Embossing pressures are variable, depending upon the desired density of the bonded areas, with 1,000 psi to 5,000 psi embossing pressures being typical.

The field embossed patterns typically comprise spaced apart embossed areas such as dots, intersecting lines or elongated bars. Preferably, for towels of the present invention, about 3% to 20% of the surface, and most preferably about 4% to 5%, of the article is embossed with field patterns. However, for some applications, lesser or greater amounts of embossing may be provided.

Figure 4:
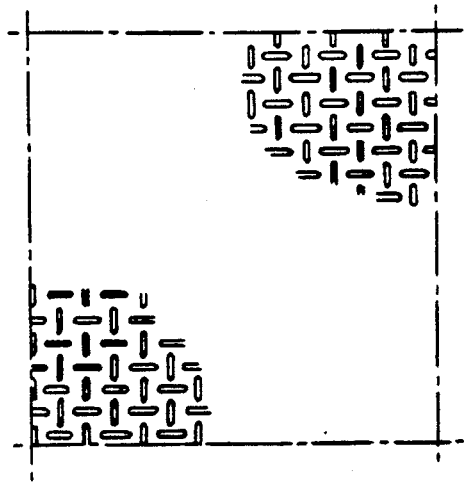
FIGS. 4a and 4b are plan views of the surface of one form of embossing roll used in manufacturing towels of the present invention.
Figure 4A:
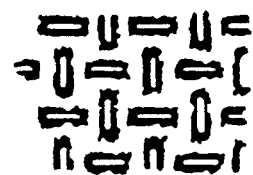

Also, a pattern of contacts in the form that would be left by the raised areas of a screen have proven particularly suitable. FIGS. 4 and 4a (the latter figure being close to actual size) illustrate contacts 80 of an embossing roll that provide such an embossing pattern.

It has also been found that the "wipe dry" characteristics of a covering or towel wiping surface can be varied by controlling the percentage of the surface area which is embossed. In testing performed as of this time, the "wipe dry" properties of the wiping surface of the towel is improved by increasing the spacing between the embossed area. Also, by increasing the spacing between embossed areas, a coarser surface results and enhances the use of the surface in scrubbing a surface.

For purposes of this description, the term "wipe dry" refers to the percentage increase in the weight [(wet-only weight/dry weight)x 100] of a 3 inch by 3½ inch sample of material, pressed against a nonabsorbent surface by a weight of 200.15 gm, and drawn at a constant speed of 50 inches per minute, a distance of 14 inches through a puddle of 10 ml of deionized water on the surface. The water is located 5 inches from the sample at the time the motion is started. In this test, 2½"×2½" inch section of the material is held by the weight against the surface and the leading and side edges of the sample are not immersed in the liquid. The leading edge in this context refers to the edge which leads in the direction of travel of the weight during the test.

Typical "wipe dry" characteristics of towels manufactured in accordance with the present invention range from about 300 to about 800 percent and are preferably about 300–500 percent. Also, different embossing patterns can be used on the respective cover surfaces. For example, a towel can be produced with a first surface with a "wipe dry" characteristic for use in more difficult scrubbing of a surface and for mopping up relatively large amounts of water. At the same time, the other surface can be provided with a smoother texture and lower "wipe dry" characteristics for final drying or wiping operations.

The Z direction tensile strength of articles formed in this manner is enhanced by the embossed areas and by the thermobonded core. In addition, by embossing all or sections of the eventual peripheral edge margins of the article, the tensile strength of the article in X, Y and Z directions is substantially improved, especially at the edge. In addition, a densified peripheral edge margin impedes the leakage of liquid from the pad through the edge.

Following embossing, the articles may be separated from the composite material. Although the articles can be die cut or otherwise separated in the manufacturing line following embossing, in the illustrated approach the articles are separated from the composite materials at a cutting location separate from the line. A laser, die, waterknife or other cutting mechanism 100 is used to separate the composite materials into pads 102 which contain the articles defined by the peripheral edge margins embossed thereon. Plural relief areas, for example 84, 86, are defined by the roll 74 such that the roll can be used to form plural towels from the composite web. The separate pads 102 are then stacked in a bin 104 for subsequent transportation to a cutting zone where the finished articles are severed from the pads.

Optional pin register defining contacts (not shown) may be included on feature roll 74. These contacts form corresponding bonds on the individual pads 102. These latter bonds may be registered with pin 110 of bin 104 so that the individual pads 102 are aligned in the bin. More than one of the aligned pads can then be cut at a time at the cutting location with the pads being held in position by pins inserted through the bonds defined by contacts 108. Other pad alignment mechanisms can also be used. Also, individual pads may be cut rather than cutting the pads in stacks.

Adhesive applicators, such as shown in dashed lines at 114 in FIG. 1., may be used to apply an adhesive coating to the surface 60 of the core or directly to the backing sheet 56 to secure the sheet 56 to the core. A similar adhesive applicator may be used to apply adhesive to secure the face sheet to the core if the face sheet 24 is secured other than by passing the face sheet through the thermobonder or embossing rolls. For enhanced durability and ease of manufacturing, thermobonding of both cover sheets to the core, followed by embossing, is preferable. Although the cover sheets 24, 56 may be secured solely by embossing, this reduces the durability of the resulting towels.

A wide variety of adhesive binders can be used for this purpose. For example, thermoplastic resin adhesives and aqueous latexes are suitable. Ethylene/vinyl/acetate copolymer is one form of suitable adhesive binder. In addition, pressure sensitive adhesives are also suitable.

The desired articles are cut from the pad sections 102 by a cutting mechanism such as a die, laser, or water knife. A suitable water knife cutting system is shown schematically in FIG. 3. Devices using a water knife, sometimes called a fluid jet, for cutting strip-like material are known. U.S. Pat. No. 4,620,466 of Jumel et al. describes one such device. Similarly, a water knife may be used in conjunction with a cutting system sold under the brand name GerberCutter by Gerber Garment Technology, Inc. of South Windsor, Conn.

Figure 3:
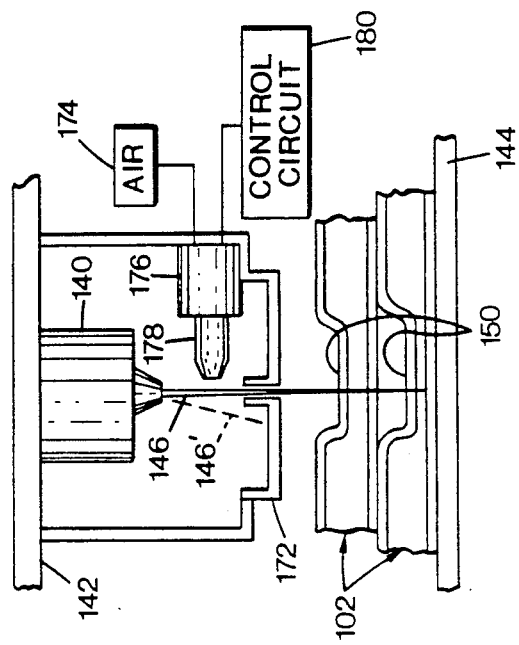
FIG. 3 is a schematic illustration of one embodiment of an apparatus for cutting towels during manufacture thereof.
Figure 2:
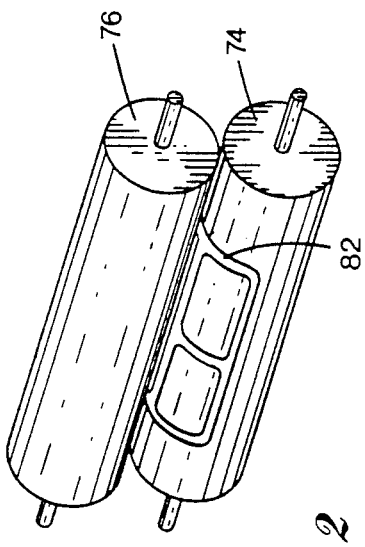
FIG. 2 is a perspective view of a pair of embossing rolls which may be utilized in compressing and heat sealing the peripheral edges of towels made in accordance with the present invention.

With reference to FIG. 3, a water knife 140 is supported by a computer controlled movable support, such as found in the GerberCutter apparatus or the cutting machine of the aforementioned Jumel et al. patent. One or more pad sections 102 to be cut are positioned on a table 144. The table is capable of moving the pads in a direction perpendicular to the direction that the water knife is moved by support 142. This combination of motion, as described in the Jumel et al. patent and in the analogous GerberCutter system, allows any arbitrary shaped article to be cut from the pad sections 102. A water stream 146 from water jet 140 severs the articles. To stop a particular cut, the water jet stream 146 is deflected by air, to a position shown in dashed lines at 146' and to a drainage trough 172. Air for deflecting the water knife is provided by a source 174 through a valve 176 and to an air nozzle 178. The valve 176 is controlled by a control circuit 180 to open and close the valve as required. The position of the cut may be controlled to be within the densified edge margin of the article, or just outside of the densified edge margin, or a combination thereof. If the article is severed from the pad outside of the densified edge margin, a softer edge is produced.

Figure 5:
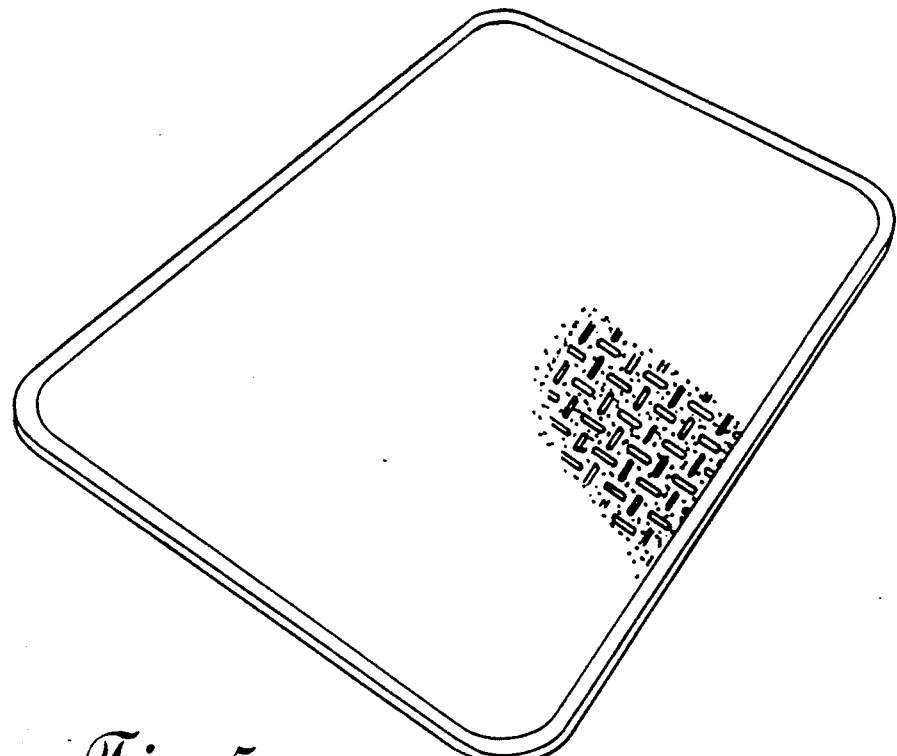
FIG. 5 is a perspective view of one form of a towel in accordance with the present invention with only a portion of the towel shown with the resulting surface texture.

FIG. 5 illustrates one example of a towel 183 of the present invention manufactured as described above. Only a portion of the towel is shown with a surface texture of the type resulting from embossing the towel with a screen or embossing rolls having a pattern of embossing contacts such as 80 in FIG. 4. The cover stock shown in the FIG. 5 illustration is apertured as indicated by the small apertures 184 in this figure. The deeper embossed areas formed by the embossing contacts 186 are indicated at 186.

The manufacture of one specific towel in accordance with the present invention is described below with the various characteristics and properties of this towel being indicated.

The specific exemplary towel had a core comprised of 20% by weight Kodel ® 410 fibers and 80% by weight wood pulp fibers. The specific wood pulp fibers utilized in this example were in NB-316 fibers available from Weyerhauser Company. These fibers were mixed and thermobonded using Sontara ® 8010 cover layers at opposite sides of the core. The core had a basis weight of 100 g/m². In addition, the basis weight of this specific Sontara ® material was 1.3 ounces per yd². The top surface was positioned adjacent to a ⅛ inch mesh screen while the bottom surface was positioned adjacent to a ¼ inch mesh screen. The sandwich of materials was pressed at 600 psi at 320° F. for 2 minutes.

The following properties were observed. For comparison purposes, the corresponding properties of a 100% cotton bar towel are also listed.

| Characteristic | Example Towel | Bar Towel |
| --- | --- | --- |
| Basis Weight (g/cm²) | 219 | 293 |
| Density (g/cm³) | 0.127 | 0.175 |
| Bulk dry (cm³/gm) | 7.88 | 5.72 |
| Bulk wet (cm³/gm) | 1.34 | 1.53 |
| Demand Absorbency ml/gm | 3.65 | **** |
| Liquid Migration rate (cm²) | 180 | 232 |
| Machine direction tensile strength dry (Nm/gm) | 24.5 | 18.1 |
| Cross machine direction tensile strength dry (Nm/gm) | 6.32 | 15.8 |
| Machine direction tensile strength wet (Nm/gm) | 25.4 | 21.7 |
| Cross machine direction wet (Nm/gm) | 6.85 | 18.8 |
| Z direction tensile strength dry (kN/m²) | 29.8 | 94.6 |
| Wicking-machine direction | 11.3 | 6.91 |
| Wicking-cross machine direction | 13.9 | 6.85 |
| Handle (gm) | 81 | 4.36 |
| Wipe dry top surface (%) | 363 | 434 |
| Wipe dry bottom surface (%) | 433 | 424 |

In the above examples, the basis weight can be determined using Tappi T-410 OM method (Tappi being the Technical determined using Tappi T-410 OM; the bulk was determined using Tappi T-426 WD; the cross machine and machine direction tensile strength can be determined using Tappi T-494; the Z direction tensile strength can be determined using Tappi T-506; the handle can be determined using Tappi T-498 SU-66; the demand absorbency can be determined using ASTM-D535 (ASTM referring to the American Society of Testing Materials); and the liquid wicking rate can be determined using Tappi T-451 (UM451). The liquid migration rate was determined by pouring 10 ml of liquid onto the center of a 40 cm × 40 cm sample. After two minutes, the length and width of spreading of the liquid was measured and the area to which the liquid spread was determined to be the migration area. The liquid wicking rate can be determined using Tappi T-451 (UM451).

As can be seen from the above example, the use of a ⅛ inch mesh screen against one of the wiping surfaces (the top surface) and a ¼ inch screen against the other of the wiping surfaces (the bottom surface) produces a towel with differing wipe dry characteristics. That is, the wipe dry characteristics of the bottom surface were higher than the wipe dry characteristics of the top surface. In some other tests, when the same size mesh screens were used at each side of a towel, the wipe dry characteristics were approximately the same at each of the towel surfaces. Thus, by controlling the embossed area of the particular surfaces, the wipe dry characteristics can be controlled to vary these characteristics, or maintain them approximately equal.

Towels produced in accordance with the above example held up during laundering repeated times. For example, on average, these towels could be machine washed and dried five or more times while still maintaining their desired characteristics.

Having illustrated and described the principles of our invention with reference to several preferred embodiments, it should be apparent to those of ordinary skill in the art that such embodiments may be modified in detail without departing from such principles. We claim as our invention all such modifications as come within the true spirit and scope of the following claims.

We claim:

1. A towel with first and second side surfaces comprising:
   an absorbent core comprising a mixture of plural types of fibers, at least one of the fibers being heat bondable, the core being heat bonded and having a basis weight of from about fifty to one hundred and fifty g/m², the heat bondable fibers of the core being present in an amount of from about 15% to 30% of the total dry weight of the core;
   the towel having first and second cover sheets with opposed outer surfaces comprising the respective first and second side surfaces, the cover sheets being secured to the core, the cover sheets being of an apertured heat bondable material;
   the towel having a first embossed pattern on one side thereof and a second embossed pattern on the other side thereof, the second embossed pattern differing from the first embossed pattern so as to provide differing wipe dry characteristics at the first and second surfaces of the towel.

2. A towel according to claim 1 in which the embossing pattern on one of the cover sheets is more closely spaced than the embossing pattern on the other of the cover sheets so as to vary the texture and wipe dry characteristics of the two cover sheet surfaces of the towel.

3. A towel according to claim 1 having densified edges so as to form a substantial liquid barrier at the edges.

4. A towel according to claim 1 in which the first embossed pattern is formed by contact surfaces like those of a one-quarter-inch mesh screen and the second embossed pattern is formed by contact surfaces like those of a one-eighth-inch mesh screen.

5. A towel according to claim 4 having a handle of from 30 to 100 grams.

6. A towel according to claim 4 having a handle of about 80 grams.

* * * * *